United States Patent
Nourbakhsh et al.

(10) Patent No.: US 10,222,360 B1
(45) Date of Patent: Mar. 5, 2019

(54) HOME AIR QUALITY ANALYSIS AND REPORTING

(71) Applicant: Airviz Inc., Pittsburgh, PA (US)

(72) Inventors: Illah Nourbakhsh, Pittsburgh, PA (US); Michael Taylor, Pittsburgh, PA (US); Christopher Bartley, Pittsburgh, PA (US); Joshua Schapiro, Pittsburgh, PA (US)

(73) Assignee: AIRVIZ INC., Pittsburgh, PA (US)

( * ) Notice: Subject to any disclaimer, the term of this patent is extended or adjusted under 35 U.S.C. 154(b) by 260 days.

(21) Appl. No.: 14/990,886

(22) Filed: Jan. 8, 2016

Related U.S. Application Data (60) Provisional application No. 62/104,382, filed on Jan. 16, 2015.

(51) Int. Cl.
  *G01N 33/00* (2006.01)

(52) U.S. Cl.
  CPC ..... *G01N 33/0075* (2013.01); *G01N 33/0062* (2013.01)

(58) Field of Classification Search
  CPC ........... G01N 33/0075; G01N 33/0062; G01N 1/2273; G01N 2291/0215; G01N 33/0004; G01N 2001/2223
  USPC ............................................. 73/31.01–31.03
  See application file for complete search history.

(56) References Cited

U.S. PATENT DOCUMENTS

| | | | |
|---|---|---|---|
| 4,375,667 A | 3/1983 | Buchan | |
| 5,467,189 A | 11/1995 | Kreikebaum et al. | |
| 6,104,299 A * | 8/2000 | Brusseaux | G01N 33/0075 194/205 |
| 6,502,469 B2 | 1/2003 | Lawless | |
| 6,693,546 B2 | 2/2004 | Skardon | |
| 6,701,772 B2 * | 3/2004 | Kreichauf | G08B 21/12 73/23.2 |
| 7,389,158 B2 | 6/2008 | Desrochers et al. | |
| 8,009,290 B2 | 8/2011 | Unger | |
| 8,085,145 B2 | 12/2011 | Fu et al. | |
| 8,147,302 B2 | 4/2012 | Desrochers et al. | |
| 8,150,465 B2 | 4/2012 | Zhang et al. | |
| 8,161,830 B2 | 4/2012 | Boudries et al. | |
| 8,204,786 B2 | 6/2012 | LeBoeuf et al. | |
| 8,441,635 B2 | 5/2013 | Schubert et al. | |
| 8,813,583 B2 | 8/2014 | Kilps et al. | |

(Continued)

OTHER PUBLICATIONS

U.S. Appl. No. 14/684,542, filed Apr. 13, 2015.

*Primary Examiner* — Daniel S Larkin
*Assistant Examiner* — Anthony W Megna Fuentes
(74) *Attorney, Agent, or Firm* — K&L Gates LLP (57) ABSTRACT

Computer-based systems and methods characterize indoor air quality in a particular building having multiple locations therein. The system comprises a back-end data center, at least one indoor air quality sensor located inside the particular building, and a graphical display device. The indoor air quality sensor(s) transmits time-stamped air quality readings collected by it to the data center via a computer network. The data center computes spatiotemporal air quality measures for the particular building based on the time-stamped air quality readings from the indoor air quality sensor(s) and transmits the computed spatiotemporal air quality measures to the graphical display device for display to the user/resident.

17 Claims, 7 Drawing Sheets

(56) References Cited

U.S. PATENT DOCUMENTS

| | | | | |
|---|---|---|---|---|
| 2003/0051023 | A1* | 3/2003 | Reichel | G01N 33/0075 709/223 |
| 2010/0305917 | A1* | 12/2010 | Takahashi | G01K 7/42 703/2 |
| 2010/0321463 | A1* | 12/2010 | Weinstein | H04N 5/76 348/14.01 |
| 2012/0154348 | A1* | 6/2012 | Okuno | C12Q 1/06 345/204 |
| 2014/0266712 | A1* | 9/2014 | Bobo | G06Q 10/08 340/539.26 |
| 2014/0281479 | A1* | 9/2014 | Gettings | G01N 33/0062 713/150 |
| 2015/0096352 | A1* | 4/2015 | Peterson | G01N 27/02 73/31.02 |

* cited by examiner

HOME AIR QUALITY ANALYSIS AND REPORTING

PRIORITY CLAIM

The present application claims priority to U.S. provisional application Ser. No. 62/104,382 filed Jan. 16, 2015, which is incorporated herein by reference in its entirety.

BACKGROUND

The present invention relates to the estimation and reporting of overall air quality inside a home, and in particular to the inference of air quality based on a combination of temporally indexed air quality values, additional environmental and behavioral home context and computational analytics.

Significant bodies of research indicate that cumulative, personal exposure to fine particulates (i.e. PM2.5) is strongly correlated with pulmonary disease and cardiovascular disease. PM2.5 is defined as the aggregate measure, by weight, of all fine and ultrafine particulate pollution in the air, with particle sizes 2.5 microns and below. PM2.5 is typically measured as micrograms per cubic meter. PM2.5 is measured in a federal regulatory manner by collecting 2.5 micron and smaller particles in a filter, then measuring the change in weight of the filter paper. Additionally, particles are counted, typically in particles per liter, by measuring the scattering of collimated light in a dark chamber off individual particles.

In addition, statistically significant correlations have now been discovered between exposure to PM2.5 by pregnant women and the onset of autism and attention deficit hyperactivity disorder in children. The residential home represents a large portion of a person's overall exposure profile to PM2.5, and therefore direct measurement and reporting of home air pollution can provide valuable insight into mitigation of overall fine particular exposure in order to maximize long-term and short-term health. The existing state of the art in fine particulate measurement provides instantaneous readings in particle counts per volume or in particle mass per unit volume. Numerous devices provide such information, for instance using light-based scattering and using impactors that embed desired particle sizes on a substrate suitable for direct optical measurement. Such instantaneous readings are dominated by the influence of human activity in the home, and therefore the state of the art fails to provide authentic measures of the home's true air quality as a system value. Other instances in the state of the art avoid direct reporting of instantaneous values, instead providing either direct feedback-based control of air handling units or providing direct ventilation recommendations to the resident. Neither of these types of solutions presents residents with interactive, spatiotemporally explorable data regarding air quality values in order to empower the resident to employ experimentation, observation and reflection to improve indoor air quality over the long term. Furthermore the state of the art fails to provide such insight in the context of comparing indoor particulate values analytically with nearby, outdoor particulate values to ascertain the effectiveness of home air pollution remediation techniques. Existing techniques use indoor and outdoor measured values to generate ventilation control commands and recommendations but fail to present indoor/outdoor air pollution differentials directly to the resident in spatiotemporally explorable formats in order to provide insight regarding the home's air quality health as compared to ambient pollution state. Furthermore the state of the art fails to perform temporal and spatial trending analysis, comparing the current air pollution levels inside the home to past values over multiple temporal resolutions, nor comparing the current and past air pollution levels of the home to other homes in the spatial vicinity. Finally, existing air pollution monitoring techniques fail to provide interfaces and analytical methods affording the user the ability to annotate behavioral context (e.g. the purchase and installation of air purifiers in the home; the cleaning of HVAC systems) and then assess the effectiveness of such interventions over short- and long-term temporal spans.

SUMMARY

In one general aspect, the present invention is directed to computer-based systems and methods for characterizing indoor air quality in a particular building having multiple locations therein, such as a user's (or resident's) home or other building of interest. The system comprises a back-end data center, at least one indoor air quality sensor located inside the particular building, and a graphical display device. The graphical display device can be integrated with an indoor sensor (thereby forming a composite air quality sensor/graphical display device) or it could be a separate, network enabled computer device, such as a smartphone, tablet, laptop, etc. The indoor air quality sensor(s) transmits time-stamped air quality readings collected by it to the data center via a computer network. The data center computes spatiotemporal air quality measures for the particular building based on the time-stamped air quality readings from the indoor air quality sensor(s) and transmits the computed spatiotemporal air quality measures to the graphical display device via the computer network for display to the user/resident.

The indoor sensor(s) can employ light reflection-based particle counting because this approach has the lowest cost point for sufficiently accurate measurements. Further, the system can employ data from outdoor air quality sensors, such as federal or municipal outdoor air quality sensors, in its computations and analysis of the air quality in the user's/resident's home.

These and other benefits of the present invention will be apparent from the description that follows.

FIGURES

Various embodiments of the present invention are described herein by way of example in connection with the following figures, wherein.

DESCRIPTION

Figure 1:
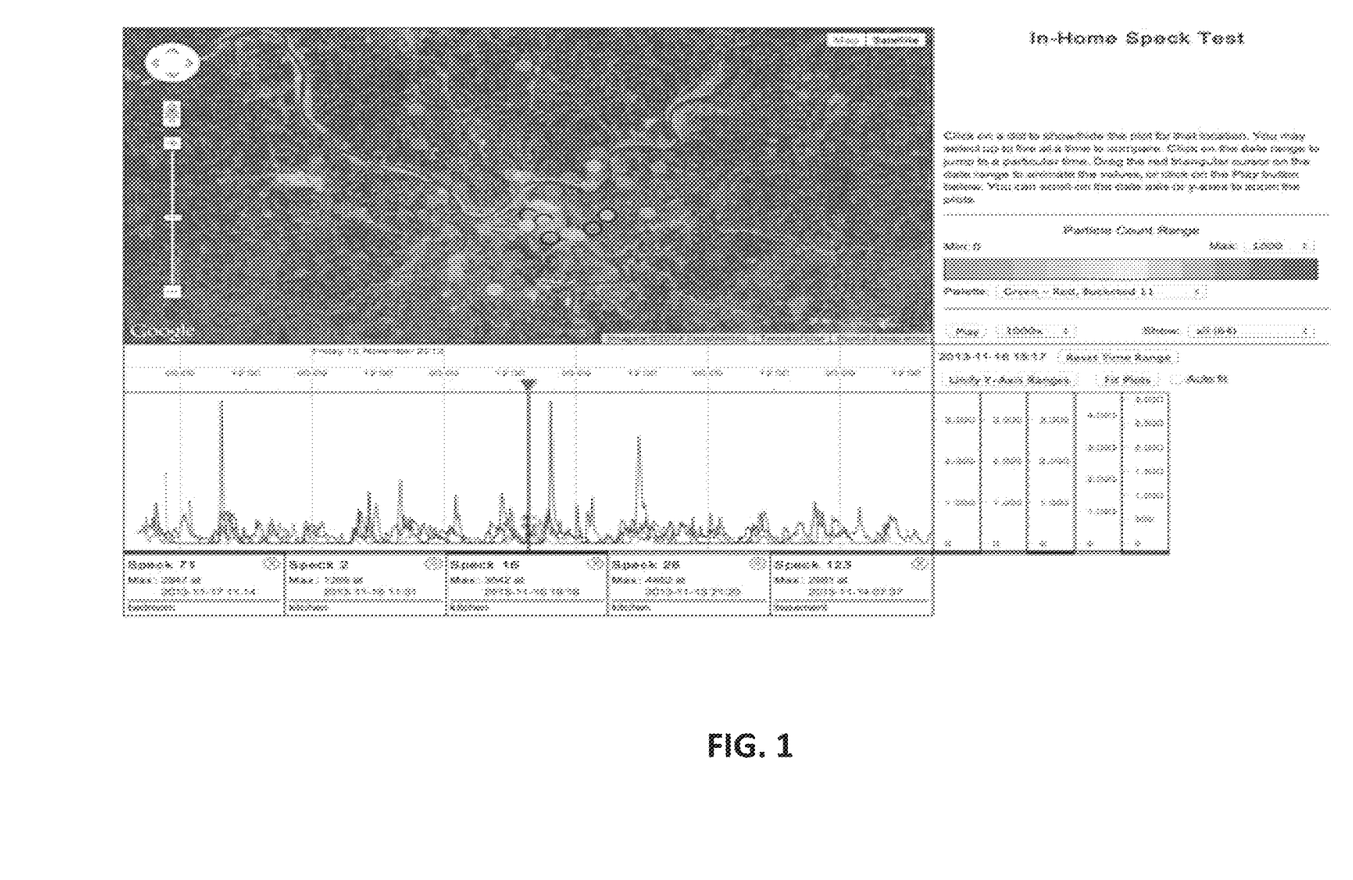
FIGS. 1, 2, 6 and 7 are example screen shots that can be provided to a home resident (or user) that show air quality measurements for the resident's home (or other building of interest) according to various embodiments of the present invention.

The present invention relates to the capture of real-time air quality point measurements in the home, combined with on-line analysis, yielding meaningful and actionable information about home air quality. The local measurement device, in one preferred embodiment, uses light reflection-based particle counting because this approach has the lowest cost point for a sufficiently accurate measurement principle, and provides direct feedback to the home residents through an interactive screen. All data is stored using an on-line server, and all data analytics are performed at the server level, where the system has access to geographically relevant indoor and outdoor air quality readings. U.S. Pat. No. 7,389,158 teaches the use of an on-line server to store air quality information, but limits feedback to an Artificial-Intelligence based recommendation generation system, whereas the present invention enables all on-line stored air quality trends and patterns to be directly observable by the resident as shown in the example screen shots of FIGS. 1 and 2 that can be provided to a user per embodiments of the present invention as described herein.

Users' mobile devices also provide equivalent feedback and visualization functionality because all data and analyses are stored and served on-line. With access to temporally fine-grained home sensor data, server-side algorithms calculate the dynamics of air quality values over time in the home. The invention's algorithms store all air quality data with time and spatial indices using a pyramidal resolution-sampling approach, storing and serving data at successively coarser temporal and spatial resolution in real time because all resolution levels are pre-computed during data storage operations. Furthermore statistics regarding baseline air pollution levels and recovery rates from local air pollution peaks are computed across moving windows of data at the finest level of temporal granularity, then resolved into coarse-resolution representations for real-time access. This is particularly important because a small sample of air quality readings is dominated by human activity in the home. Statistical analysis of the data fluent over time yields rest state minima, demonstrating the best possible air quality of the home when human activity is not present; frequency spectra, capturing periodic components of air quality change in the home, for instance diurnal and forced-air system behavior; response behavior to poor air quality spikes when caused by exogenous events including cooking and outdoor pollution infiltration through open doors and windows.

The server also maintains time-indexed, nearby outdoor air quality values as well as other local indoor air quality comparables, enabling the statistical analysis to include long-term differential comparisons of the home's air pollution level compared to ambient, outdoor levels and nearby, comparable homes. Server-based statistical analysis yields both single-valued estimates of overall home air quality health and temporal trending analysis, indicating the overall health of the home over time. All such statistical reports are available for review by the homeowner using the measurement device's local screen and using their own mobile devices. For example, typical Pittsburgh residence PM2.5 values range from 9 micrograms per cubic meter during evening rest times to 35 micrograms per cubic meter during active days, and up to 50 micrograms per meter during high-pollution inversion layer days. Rest state minimum 48 hour sliding window PM2.5 statistics will reveal a spread between 7-9 micrograms minimum during healthy periods of the month, up to 20-30 micrograms during unhealthy periods.

The server also retains contact information for the home user, enabling out-of-band air quality analytical results to trigger direct notification of the user, encouraging immediate actions to mitigate poor home air quality.

The invention also enables the user to annotate and label events and data, marking critical actions that affect home air quality so that the system may evaluate the effectiveness of these resident actions. Examples of such actions include: replacement of the HEPA filter in the home forced-air system; cleaning of the home's ductwork; purchase and placement of a particulate capture device in the home; removal or replacement of floor-to-floor carpeting; replacement of the HEPA filter in a particulate capture device. Server-side statistical analysis then measures and reports the efficacy of actions taken on computed home air pollution health. Referring to process flow in FIG. 4, described further below, air pollution measurement data is transmitted to servers (steps 201 and 202), the server measures rest state air pollution in the home (step 203), the user observes rest state home air pollution levels (step 204), the user replaces HEPA filter in home purifier and annotates this change (step 206) then observes the change in measured and reported rest state air pollution (repeating steps 201, 202, 203, 204).

The present invention also enables the user to map air quality variation throughout the home using two techniques, for example. First, a single measurement device may be moved within the home to multiple locations, for instance to parent's and child's bedrooms. An example use case follows:

Resident places one sensor inside parent's bedroom, with air purifier running in parent's bedroom, and allows data collection for five days. Then, resident places sensor inside child's bedroom for an additional five days, annotating the move date and time on-line. In viewing the data, the resident notes that the baseline PM2.5 reading in the parent's bedroom, where the air purifier is placed, is 5 micrograms, whereas the baseline PM2.5 reading in the child's bedroom is 15 micrograms. Concerned, the parent moves the purifier to the child's bedroom, annotates the move, and measures for five more days in the child's bedroom. Noting that improved PM2.5 reading down to 5 micrograms, the resident purchases a second air purifier specifically for the child's bedroom.

In the second technique, multiple measurement devices may be placed within the home in parallel, and annotated as such, enabling the collection of differential air quality values throughout the home in parallel. An example use case follows:

Resident places one air quality sensor in the kitchen, and a second in the infant's nursery. Both are coupled to tag names in the server and graphed simultaneously as shown in the figure above. After five days of measurement, the resident reviews, graphically, the simultaneous plots and, setting the y axes to the same scale, notes that increases in kitchen air pollution lead almost immediately to heightened pollution in the child's bedroom, which his located above the kitchen. The resident makes more liberal use of the kitchen hood extraction fan based on on-line recommendations, and notes the decreasing plumes of air pollution in the child's nursery subsequent to this behavioral change.

Existing state of the art does employ multiple sensors within a single indoor area, but fails to appreciate the variability in indoor air quality within a single enclosure. For example deploying multiple air quality sensing nodes, but combining all such nodes into a single air quality index for the indoor space, failing to evaluate and report the variability in air quality spatiotemporally in the target location.

Figure 3:
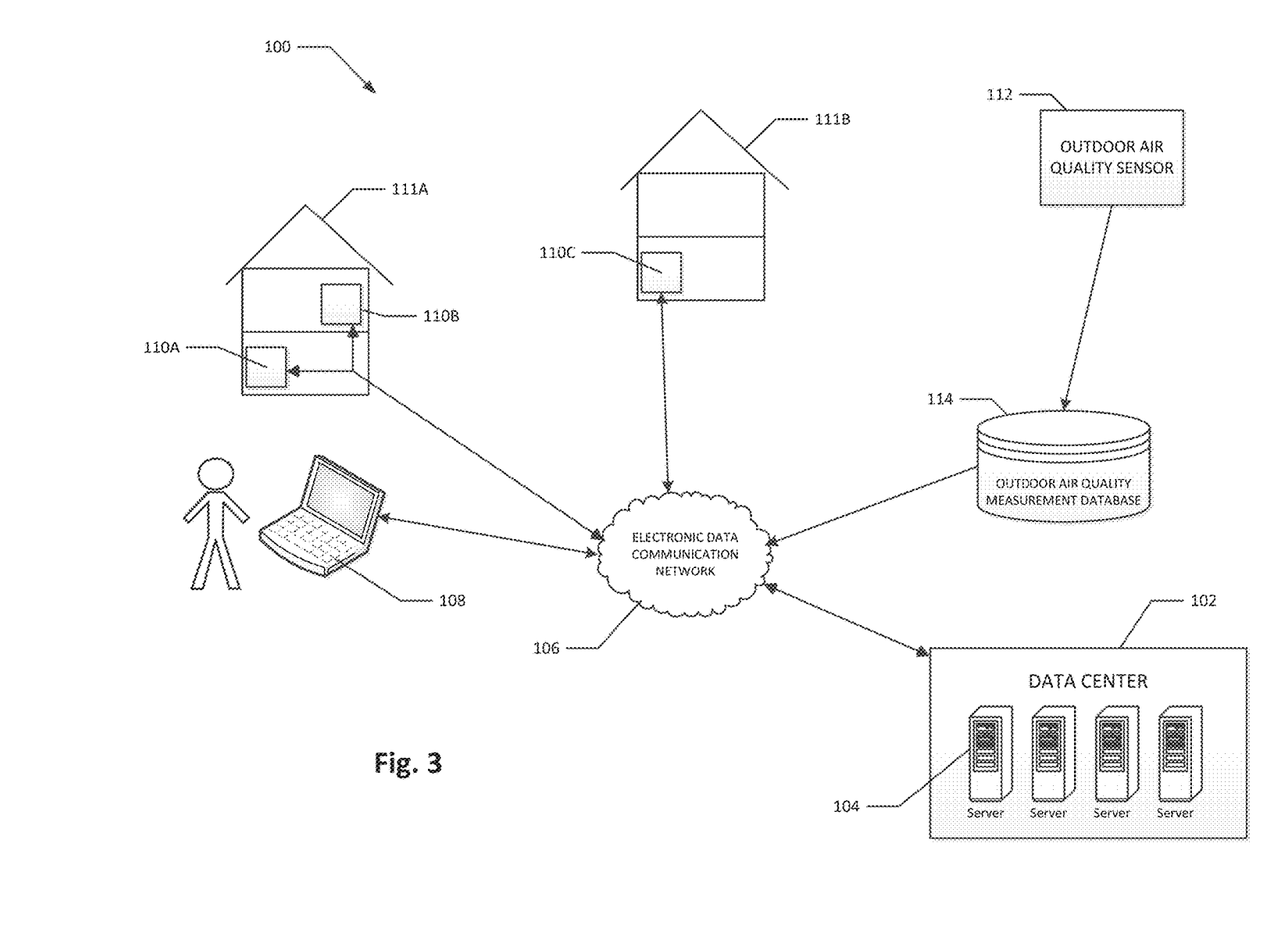
FIGS. 3 and 5 are diagrams of systems for analyzing and reporting air quality for the resident/user according to the various embodiments of the present invention.

FIG. 3 illustrates an embodiment of the air quality measurement device-server architecture or system 100 suitable for implementing the home air quality analysis and reporting system. In the illustrated example shows two indoor air quality sensors 110A, 110B in a first house 111A, and a third indoor air quality sensor 110C in a second house 111B. The system also includes numerous outdoor air quality sensors, one of which 112 is shown in the diagram for the sake of simplicity. The outdoor sensors 112 could be part of a federal and/or municipal network of air quality sensors, and the illustrated one 112 is the federal/municipal outdoor sensor that is geographically closest to the house 111A. A data center 102, comprising one or a number of computer servers 104, is in communication with the sensors 110A-C, 112 via an electronic data communication network 106. The server(s) 104 of the data center 102 maintain (i.e., store) all reported real-time air quality sensor data from all sensors 110A-C, 112. In various embodiments, the air quality measurement data from the outdoor sensors 112 may be stored in one or more online databases 114 that the data center access to access the outdoor sensor's air quality measurement data. The server(s) 104 of the data center 102 further perform the computational air quality analytics described below. The data center 102 is bidirectionally in communication with the indoor air quality sensors 110A-C via the network 106. Also, as shown in FIG. 3, the data center 102 is in communication with a mobile device 108 associated with the user via the network 106. The mobile device 108 could be a laptop, a table, a smartphone, or any other suitable mobile computing device. The data center 102 can deliver the analytics to the mobile device 108 via the network 106, and/or deliver them to one of the indoor sensors 110A-C that have a graphical display device suitable for displaying the analytics. As mentioned above, the indoor sensors 110A-C preferably include light-reflected based particle counters. An example of a suitable indoor sensor 110A-C is the Speck® air quality sensor from Airviz of Pittsburgh, Pa. More details about suitable indoor air quality sensors can be found in (1) U.S. patent application Ser. No. 14/684,542, entitled "Air Quality Sensor," filed Apr. 13, 2015 and (2) U.S. patent application Ser. No. 62/189,978, entitled "Group Calibration of Air Quality Monitors," filed Jul. 8, 2015, both of which are incorporated herein by reference.

The network 106 may be an IP network, such as the Internet, an intranet, or extranet, etc. The network 106 could also use other types of communication properties, such as Ethernet, ATM, etc., and could include wired and/or wireless communication links. The network 106 can provide wireless communication for the end user mobile device 108 and/or the indoor sensors 110A-C. It could include a cellular network or a WiFi network, for example, that connects to the publicly switched telephone network and the Internet.

Figure 2:
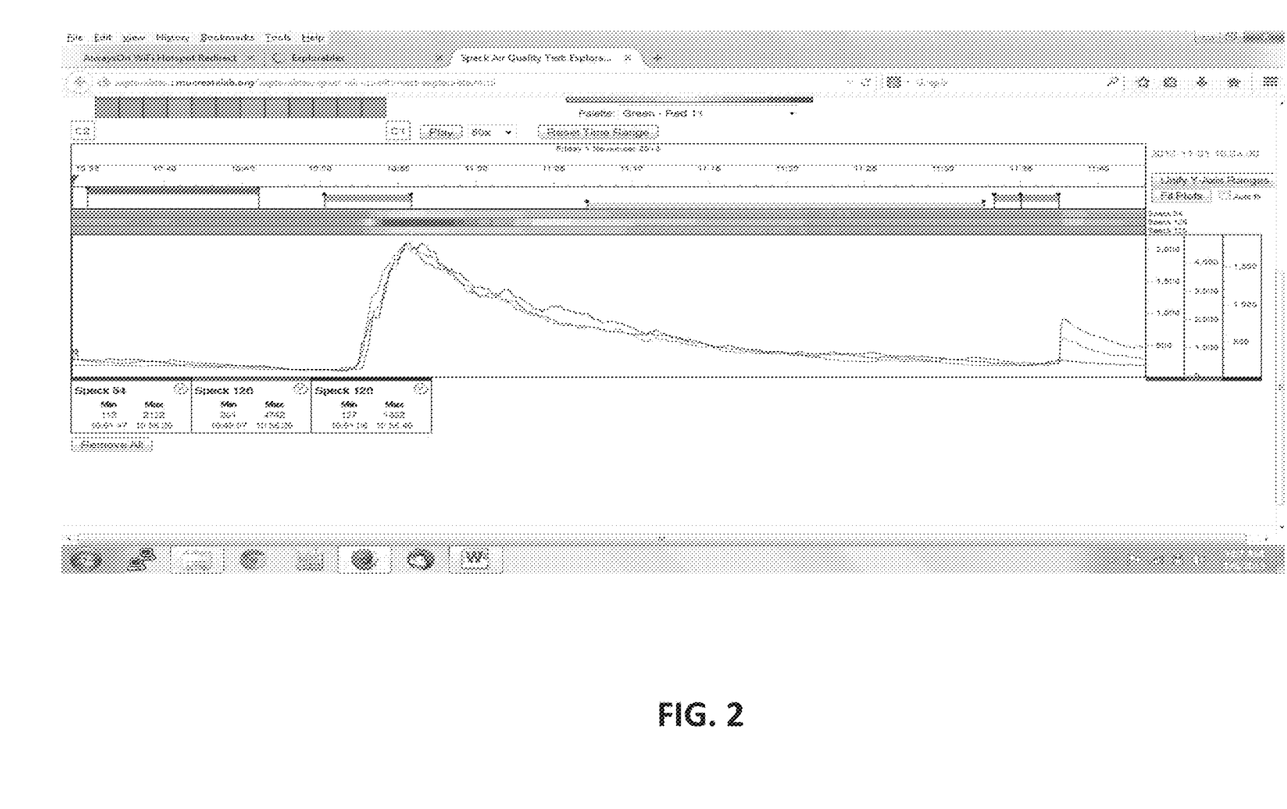

FIG. 2 is a flow diagram illustrating steps that can be implemented using the architecture 100 in accordance with an illustrated embodiment. The illustrated process starts with, at steps 201 and 202, the indoor sensors 110A-C and the outdoor sensors 112 transmitting their air pollution measurements to the data center 102. As mentioned previously, the outdoor sensors 112 could transmit their data directly to the data center 102 via the network 106, or the data could be stored in an online database 114 accessible to the data center 102. Next, at step 203, the data center 102 performs the statistical analysis for home quality analysis based on the air quality data received at steps 201 and 202. Next, at steps 204 and 205, the data center 102 transmits the home air quality analysis summary to the indoor air quality sensors 110A-C (step 204) and/or the user's/resident's mobile device 108 (step 205). Next, at step 206, the data center 102 can receive user/resident annotations regarding air quality context, as described herein. The process can then be repeated on an ongoing basis.

Figure 5:
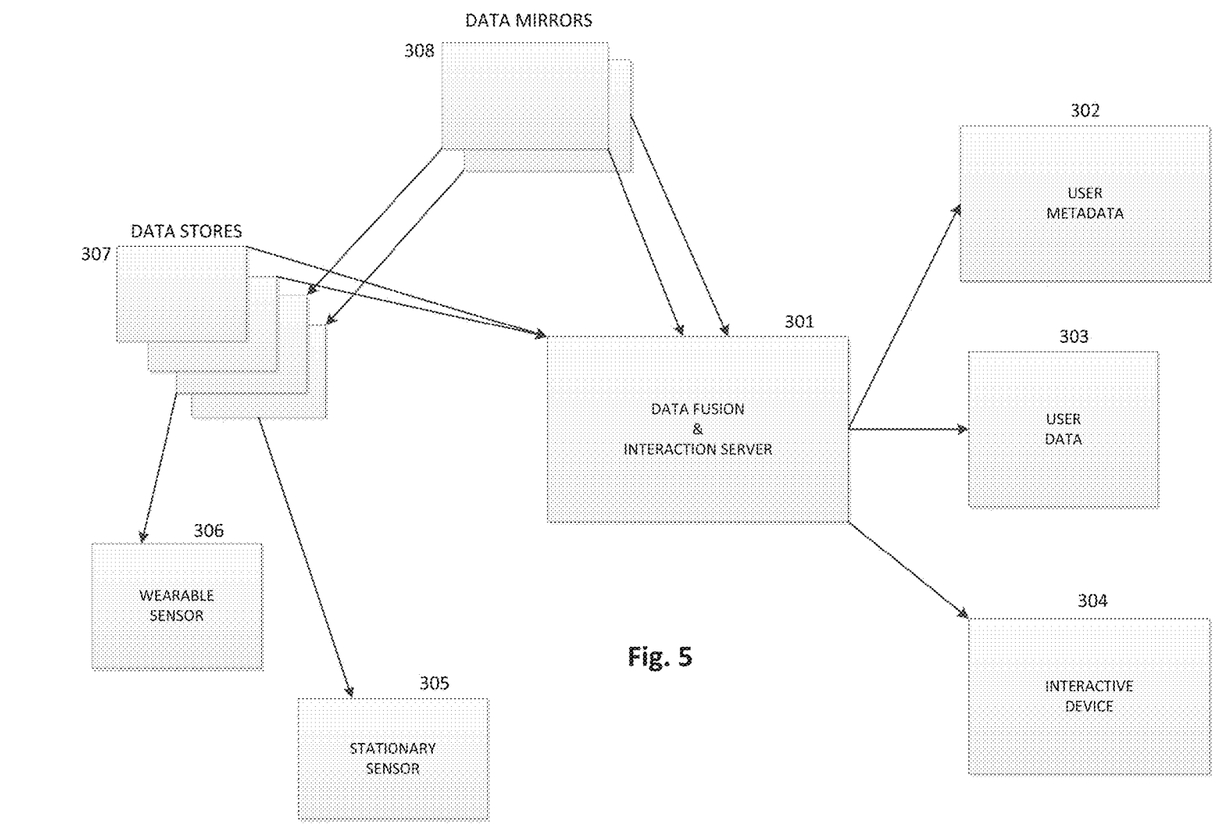

FIG. 5 illustrates an embodiment of the data fusion system, demonstrating how the system can combine air quality information, biometric data, location information and activity information into an interactive visualization of annotated, personal air pollution exposure over time and space. The data fusion and interaction server system 301 (e.g., the data center 102 of FIG. 3) performs on-line data fusion computational processing and interactive serving of personal air pollution exposure visualization and categorization using on-line communication protocols (e.g. HTTPS with OAuth authentication). User Metadata 302 stores authentication, credentials and unique identification information for each system user. User Data 303 stores fused, pre-computed data regarding individuated user air pollution exposure over time and space as well as user air pollution cumulative exposure by category of location and activity. Interactive GUI device 204 provides direct interaction affordance to a user by being served by Server 301. Handheld Internet-connected devices and desktop devices, including Android and iPhone tablets, phones and laptops that connect and offer direct data interaction are instances of Interactive GUI Device 304. Wearable sensor 306 collects air pollution, biometric, activity, and/or location information directly on the user's body. Various Fitbit, Jawbone Up and BodyMedia wearable systems can instantiate Wearable Sensor 306. Stationary sensor 305 collects air pollution and activity information at a fixed location, such as a home wall or building roof (e.g., sensors 110A-B of FIG. 3). NEST indoor sensors, Netatmo sensors, the Speck® air quality monitor from Airviz, and municipal air quality sensors are examples of the Stationary Sensor 305. Data Stores 307 store temporally tagged environmental, biometric and activity data from both Wearable Sensors 306 and Stationary Sensors 305. Data Mirrors 308 are populated with data regularly by fusing, interpreting and re-saving Data Stores 307. The Data Fusion and Interaction Server 301 is capable of accessing relevant user and contextual data both from original Data Stores 307 and from Data Mirrors 308.

Numerous wearable sensors collect, store and communicate information regarding a user's biometric data, environmental context and activity data. Such data includes heart rate, heart rate variability, GPS location, Wifi-based location, galvanic skin response, exercise start and stop times, exercise intensity, calorimetric counting, cumulative UV exposure, sleep quality, deep sleep start and stop times, local air pollution measurements, and associated values. Wearable devices report values to corporate data stores, some cases providing public interfaces for data extraction, such as Jawbone UP, and in other cases providing only non-real-time review of data at slow data rates, such as BodyMedia sensors. Mobile phones and tables such as Android devices and iPhones provide user location and user activity information directly and through executing local applications (i.e. App's). Such App's also enable the user to directly annotate context, and this manually inserted information is stored in Data Stores using the same storage and retrieval architecture and sensor-collected information. Remote access demands user-based authentication, using corporate authentication or using third-party identity verification using services such as Facebook and Google. Direct, real-time access of data stores (307) when appropriate are thus enabled by the Data Fusion Server (301) using user authentication credentials which are entered initially by users via an Interactive Device (304) such as an iPhone, and then stored as encrypted User Metadata (302). In the case of data stores without high-efficiency Application Program Interfaces for direct, high-bandwidth data access (such as NEST home monitors), Data Mirrors (308) duplicate, process and re-save Data Store information on alternative databases architected for Interaction Server's high-rate data posting processes. In one embodiment, Data Mirrors make use of MySQL for metadata structural information and Node.js for real-time insertion and extraction of data at a nearly unlimited resolution and size scale. In order to regularly access corporate Data Stores, Data Mirror mirroring algorithms use User Metadata (302) authentication credentials by requesting such credentials from the Data Fusion server (301).

Numerous stationary sensors (305) provide activity and environmental information. NEST provides user activity information, user location information, temperature carbon monoxide and carbon dioxide level information. Netatmo provides air quality information, temperature and humidity information. Another suitable stationary sensor is the Speck® air quality monitor from Air Viz. In a manner identical to that of Wearable Sensors, such stationary sensor information is stored off-board, in on-line Data Stores and is available for authenticated extraction, in some cases with sufficient efficiency for real-time, direct use by the Interaction Server and in other cases with insufficient efficiency, thus requiring implementation of a Data Mirror via authentication credentials provided by the relevant user and stored in User Metadata.

User Metadata (302) stores both direct authentication and contact information for the Personal Air Pollution Exposure interaction system, as well as authentication keys for all data stores relevant to each individual user's air pollution exposure, including their wearable sensors and the stationary sensors within their authentication scope and within their vicinity. Such metadata is stored with appropriate encryption controls to dissuade nefarious access and to protect the privacy and data rights of all system users.

Date Fusion and Interaction Server (301) provides authentication services for data mirroring, and also performs data fusion to yield annotated and classified data regarding cumulative air pollution exposure per-user. The Server computes, organizes and presents classified cumulative air pollution exposure values both in real time, as required for custom views by the Interactive Device (304), and as pre-computed results stored as User Data (303) to enable high-speed visualization and recall by the user, also through an Interactive Device (304). As one example, the user may log into the air pollution exposure system, being verified in identity via stored User Metadata, and then may visualize cumulative 2.5 micron particulate air pollution exposure over the past one month period by home and school categories. Furthermore, home air pollution exposure may be broken out into two cumulative values, one for exposure during sleep in the child's bedroom and a second for exposure during waking hours. Finally, user-annotated episodes of asthma attacks requiring inhaler doses may be shown for each of school and home categories. Such visualization affords the child's parents the ability to understand what fraction of total particulate exposure sustained by the child is due to each portion of the ritual week, and therefore what corrective actions will maximize reduction of particulate exposures that trigger asthma attacks and, thereby, poorer quality of life.

Pre-computing of such frequently requested categorizations and pre-saving of such data as User Data (303) minimize the wait time when the user makes a real-time request using an Interactive Device (304). However, it is not possible to pre-compute and store all possible data classification visualizations ahead of time. Thus the Server (301) must afford both the submission of interactive, pre-computed data as well as real-time data fusion using Data Stores and Data Mirrors as appropriate for user visualization requests.

The Interactive Device (304) functions as the principal communication link between a user and the air pollution exposure information available through the invention. The user inputs login information, contact information, credentialing information and authenticates connections to extant data services such as those provided by wearable and stationary environmental and activity sensors. All these specifications are performed using one or more Interactive Devices connecting to the Interaction Server 301. Such Interactive Devices include mobile devices through App links, browser-based secure https: links and native applications on computing devices. The user also uses Interactive Devices to provide annotations directly to the personal air pollution exposure system. This data, stored directly as User Data (303), is immediately available during visualization of air pollution exposure, both as a tertiary annotation field and as additional categories for organizing cumulative air pollution exposure. For example a manually user-entered annotation regularly marking days when a residence has distinct industrial smells from nearby manufacturing plants enables the user to organize personal exposure by showing cumulative air pollution on days so marked as compared to all other days over the past month. Such visualization would enable the user to understand whether strong industrial smell is likely to correlate with poor air pollution that leads to clearly deleterious health consequences in the long term.

The Interactive Device component also serves as the principal means by which the user creates interactive, explorable visualizations of fused data in order to comprehend cumulative air pollution exposure. Data Mirrors and User Data architectures pre-compute air pollution values indexed spatially and temporally, and insert pyramidally arranged coarse-resolution versions of all such data, enabling the Interaction Server to request and receive air pollution exposure data at exactly the resolution demanded for the specific temporal and spatial window specified by the user through the Interactive Device. This resolution match between required and recorded data maximizes the speed with which a user can request, modify and observe patterns in data across time and space without waiting for regeneration and resampling computations to take place at the server.

In an embodiment of the invention, as shown in FIG. 3, a network of indoor and outdoor air quality sensors and an Internet server infrastructure together provide the measurement, analysis and reporting of home air quality. Air quality sensors appropriate for the system include, but are not limited, to: Netatmo Weather Station, Dylos DC1100, sensors built using the Shinyei PPD24NJ particle-counting system, and the Speck® air quality monitor from Airviz.

FIG. 3 illustrates an embodiment of the system network suitable for implementing the invention's home air quality functionality. The depicted embodiment contains two air quality sensors 110A-B within a single home 111A, suitable for measuring particulate concentrations of PM2.5 on a continuous basis. The air quality sensors 110A-B can use 802.11 Wifi connectivity, via a home Wifi router (not shown), for example, to post timestamped and sensor-indexed particulate concentration values to the online servers 104. The servers 104, having already documented the registration of the home and associated serial numbers of sensors 110A-B, record and duplicate in-home particulate concentration values. The servers' database architecture can utilize Node.js Express to record all data points, with all metadata, including sensor serial number and home identity, stored as metadata using MySQL. OAuth2 can be utilized for server authentication to maximize data integrity and security. The servers 104 can scale, with Node.js, to record and rapidly extract billions of air quality data points per sensor channel. Metadata fields record home-sensor associations as well as the location of the home. Data from the outdoor air quality sensors 112, which can include the Federal AirNow network of national sensors, is mirrored in servers 104 together with location information. Using home location information, the servers 104 associate the closest federal and/or municipal outdoor air quality sensor(s) 112 with the home 111A, as foundational outdoor baseline air quality data. Finally, a third data vector is represented by indoor sensor 110C, measuring indoor air quality in a geographically nearby home 111B also being served and analyzed by the data center 102. Such secondary indoor sensors 110C can present baseline comparable data on indoor air quality statistics across indoor environments in the same geographic vicinity.

The servers 104 of the data center 102 can use scheduled data analysis background processes to compute statistical summaries of indoor air quality for each home, such as the home 111A that is served by sensors 110A-B in FIG. 3. The rest state home air pollution index can be computed by the servers 104 by applying the Minimum function on all reported data from sensors 110A-B across a moving time window, such as a 48-hour time window or some other suitable duration. This minimum value represents the rest level air pollution level in the home 111A when, due to diurnal behavior patterns, human activity is subtracted as the generator of PM2.5 plumes. The pollution recovery index can be computed by the servers 104 for the home 111A by identifying local particle count data maxima, defined as a unimodal local maxima across five hours (or some other sufficiently long time period) within a one-week sliding temporal window. For each such local maximum, the average recovery slope post-maximum to the subsequent local minimum is measured by the servers 104. The mean air pollution recovery is computed by the servers 104 as the mathematical mean of all computed recovery slopes within a sliding 24 hour time window, and median air pollution is computed similarly on a sliding 24 hour basis (or some other time period).

All statistically computed home air pollution metrics can be reported by the data center 102 to both an in-home air quality measurement sensor 110A-B by use of, for example, a local TFT touch-screen on the indoor sensor, and/or directly to the resident's mobile device(s) 108 using HTTPS-encoded web services, for example.

Figure 6:
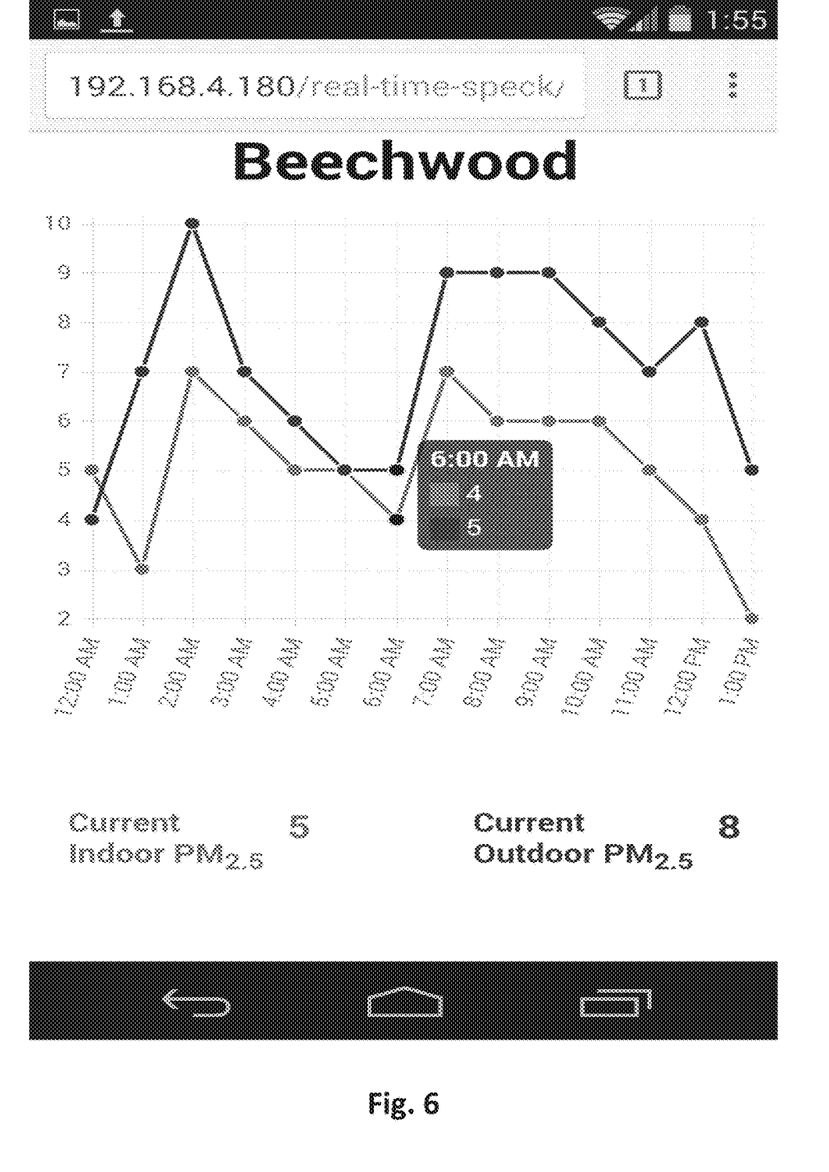
Figure 7:
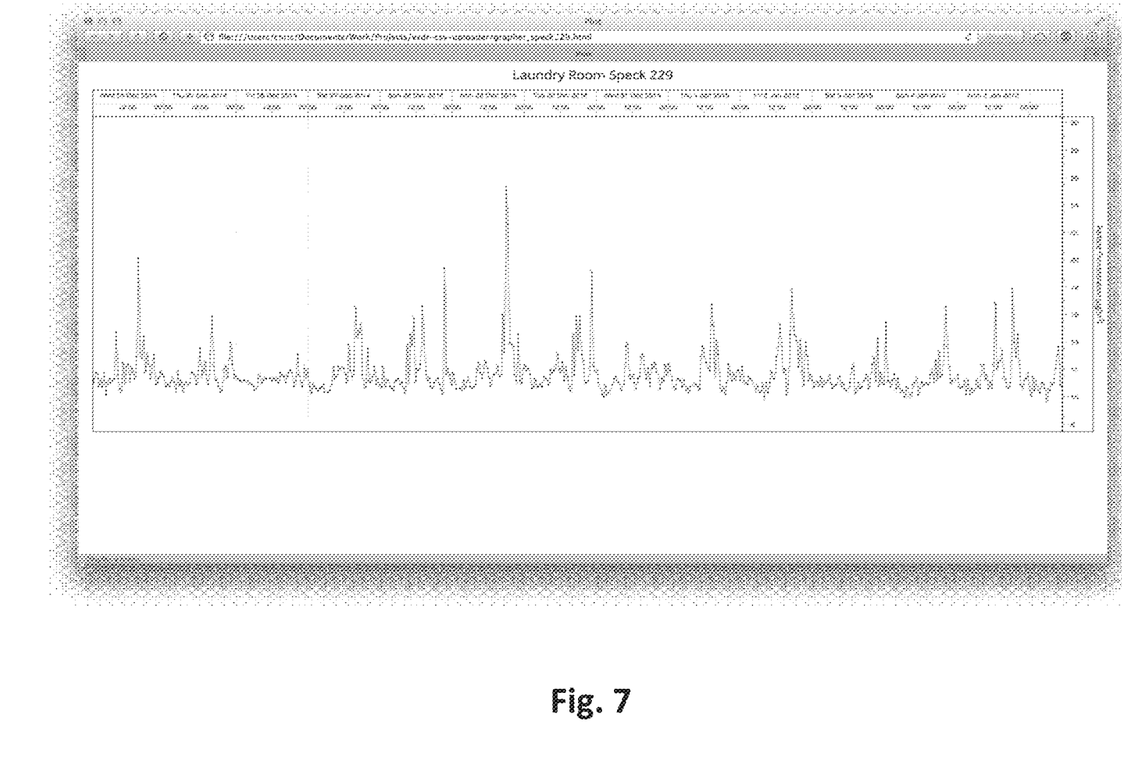

FIGS. 6 and 7 are exemplary screen shots for particle tracking over time that can be computed by the data center 102 and displayed on the user's graphical display device in accordance with various embodiments of the present invention. FIG. 6 represents data flow for the aforementioned embodiment, beginning with the acquisition of particle concentration values directly by sensors (step 201 in FIG. 4) and the mirroring of outdoor air quality sensors to the data center 102 (step 202). The statistical evaluation of sensor data (step 203) can operate periodically using server data. Statistically derived summary data can then be communicated both to in-home sensor platforms (step 204) and to the resident's mobile device (step 205). FIG. 7 shows particle concentration ($\mu g/m^3$) over time for a sensor placed in a particular location in the resident's home (the laundry room in this case).

Figure 4:
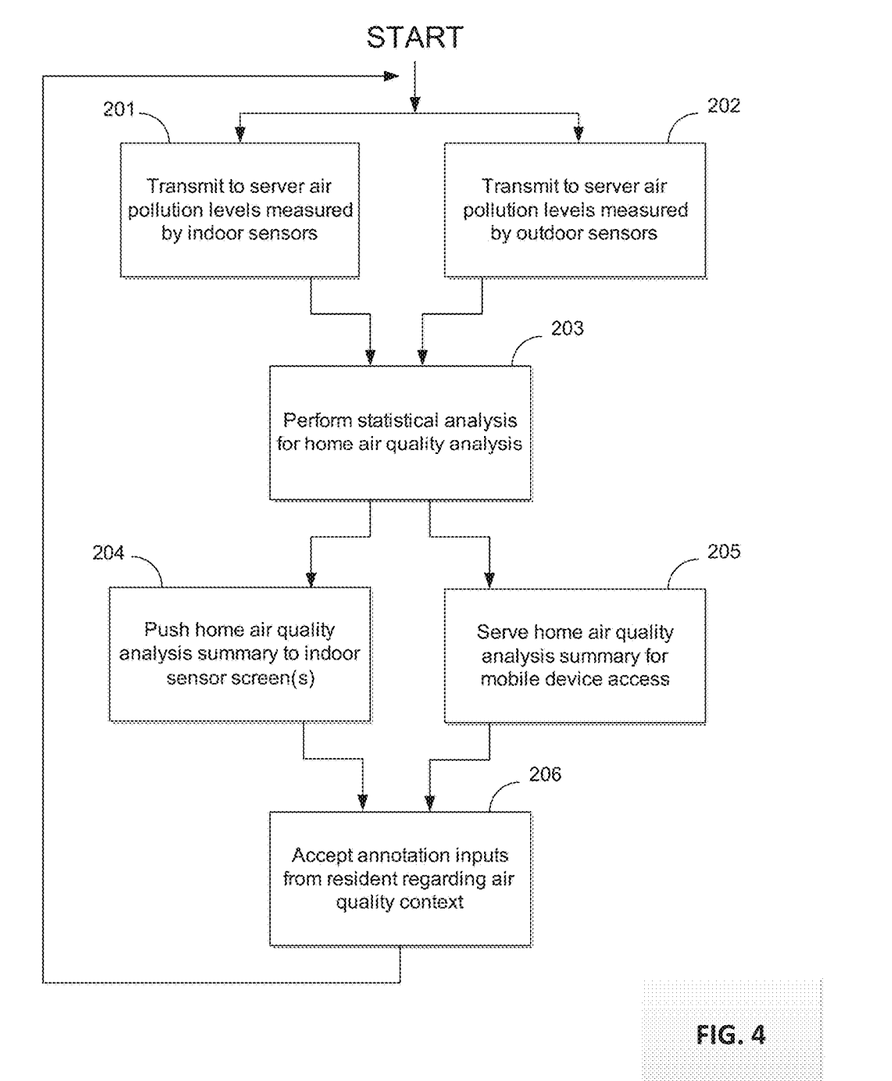
FIG. 4 is a flow chart illustrating a computerized process for analyzing and reporting the air quality measurements according to various embodiments of the present invention.

In order to empower the user/resident to discriminate and measure the impact of changes to the air pollution dynamics of the home, for instance through the replacement of a HEPA filter cartridge in an extant in-home air purifier, the data center 102 can accept user-generated annotations (step 206) from both a local sensor (such as through a TFT touchscreen of the local sensor) and/or from the resident's/user's mobile devices 108. User generated annotations, in turn, can be shown in graphical views of indoor air quality and statistically derived summary data over time, enabling the resident to compare raw and statistically derived air pollution values before and after interventions.

Statistical analysis of indoor air quality values (step 203) may make use of differential values by subtracting indoor, measured data points from outdoor nearby reported data points, enabling the resident to view raw, mean and median differences between indoor and outdoor air quality to ascertain the home air pollution health in context of the outdoor environment. Using metadata stored regarding the resident's electronic contact details, the server configuration (for the servers 104 of the data center 102) allows the resident to specify measured and differential air pollution values that trigger direct notification. With such configuration specified, the server 104 performs direct initiation of contact with the user via digital messaging when resident-specified statistical thresholds are exceeded, empowering the resident to actively manage indoor air quality.

Using the previously described annotation functionality, the resident is additionally able to specify within-home specific location details for each in-home sensor 110A-B, for each measurement time sub-segment. The server 104, in turn, can provide graphical views of raw and statistically derived air quality data together with in-home location details as annotated, enabling the resident to compare air quality not only temporally but also spatially within the domicile, for example comparing the air quality in the child's nursery with the air quality in the master bedroom, where an air purifier may be stationed.

In various embodiments, a method for evaluating the air pollution health of a building may comprise installing one or more air quality sensors 110A-B that measure and communicate to the data center 102 time-indexed air quality values within the building; implementing a server 104 collecting the air quality sensor data from the sensors 110A-B located within the building and, optionally, receiving air quality data streams from sensors 112 outside the building; statistically evaluating spatiotemporal air quality data related to the building with statistical techniques that include, at least, computing baseline air quality health statistics and air quality dynamics of the building over time and space; and/or interactively presenting air quality data and air quality building health data to users, with means operable to modify temporal resolution of air quality and building health analyses data.

Other features of the present invention may include, in any reasonable combination: PM2.5 specifically; Particle count as the sensor data (particles per liter) as an alternative to PM2.5; Specific statistics: sliding window Min( ) function; User-specified annotation that is stored and then interactively viewable with the data; explorable in varying resolution temporally and spatially; Multiresolution data pre-computation and serving; and direct comparison of multiple air pollution readings, including one or more indoor, one or more outdoor.

In one general aspect, therefore, the present invention is directed to a system for characterizing indoor air quality in a particular building having multiple locations therein. The system comprises a back-end data center 102 that comprises one or more computer servers 104; at least one indoor air quality sensor 110A-B located inside the particular building 111A, where the at least one indoor air quality sensor 110A-B transmits time-stamped air quality readings collected by the at least one indoor air quality sensor 110A-B to the data center 102 via a computer network 106; and a graphical display device. The data center 102 computes spatiotemporal air quality measures for the particular building 111A based on at least the time-stamped air quality readings from the at least one indoor air quality sensor 110A-B and transmits the computed spatiotemporal air quality measures to the graphical display device via the computer network 106. The graphic display device in turn displays the spatiotemporal air quality measures computed by the data center 102 on an interactive graphical display of the graphical display device.

In various implementations, the air quality readings from the at least one indoor air quality sensor 110A-B are PM2.5 readings. Also, the graphical display device could be combined with the at least one indoor air quality sensor in a composite air quality sensor/display device 110A-B, or it could comprise a network-enabled computer device 108 such as a personal computer, a laptop, a smartphone, a table computer, and a wearable computer device. Further, the user may supply data annotations via the graphical display device to the data center, where the data annotations might comprise data indicative of a location of at least one indoor air quality sensor located inside the particular building.

In yet other implementations, the system further comprises at least one outdoor air quality sensor 112 that is located outside and not inside the particular building 111A. The at least one outdoor air quality sensor 112 also transmits time-stamped air quality readings collected by it to the data center 102 via the computer network 106. The data center 102 can then compute spatiotemporal air quality measures for the particular building 111A based on at least the time-stamped air quality readings from the at least one indoor air quality sensor 110A-B and the time-stamped air quality readings from the at least one outdoor air quality sensor 112. For example, the data center could compute raw, time-stamped differences between the indoor sensor readings and the outdoor sensor readings. It could also compute statistical summarizations of those raw, time-stamped air quality measures over rolling time periods, such as the mean or median.

In yet other implementations, the data center computes and transmits to the graphical display device a mean and/or median air pollution recovery index value for the particular building. The data center can compute the mean and/or median air pollution recovery index value by identifying several local particle count maxima in the time-stamped air quality readings from the indoor air quality sensor over a time period; computing a post-maximum recovery slope for each of the several local particle count maxima to an immediately subsequent minimum particle count; and computing the mean and/or median of the post-maximum recovery slopes across all of the several local particle count maxima in the time window. Still further, in other implementations, the data center can continuously compute real-time air quality measures for the particular building based on the time-stamped air quality readings from the at least one indoor air quality sensor and then transmit a notification to the graphical display device via the computer network when a real-time air quality measure exceeds a pre-established threshold.

The examples presented herein are intended to illustrate potential and specific implementations of the present invention. It can be appreciated that the examples are intended primarily for purposes of illustration of the invention for those skilled in the art. No particular aspect or aspects of the examples are necessarily intended to limit the scope of the present invention. For example, no particular aspect or aspects of the examples of system architectures, user interface layouts, or screen displays described herein are necessarily intended to limit the scope of the invention.

It is to be understood that the figures and descriptions of the present invention have been simplified to illustrate elements that are relevant for a clear understanding of the present invention, while eliminating, for purposes of clarity, other elements. Those of ordinary skill in the art will recognize, however, that a sufficient understanding of the present invention can be gained by the present disclosure, and therefore, a more detailed description of such elements is not provided herein.

In various embodiments of the present invention, a single component may be replaced by multiple components, and multiple components may be replaced by a single component, to perform a given function or functions. Except where such substitution would not be operative to practice embodiments of the present invention, such substitution is within the scope of the present invention. Any of the servers described herein, for example, may be replaced by a "server farm" or other grouping of networked servers (e.g., a group of server blades) that are located and configured for cooperative functions. It can be appreciated that a server farm may serve to distribute workload between/among individual components of the farm and may expedite computing processes by harnessing the collective and cooperative power of multiple servers. Such server farms may employ load-balancing software that accomplishes tasks such as, for example, tracking demand for processing power from different machines, prioritizing and scheduling tasks based on network demand, and/or providing backup contingency in the event of component failure or reduction in operability.

Various embodiments of the systems and methods described herein may employ one or more electronic computer networks to promote communication among different components, transfer data, or to share resources and information. Such computer networks can be classified according to the hardware and software technology that is used to interconnect the devices in the network, such as optical fiber, Ethernet, wireless LAN, HomePNA, power line communication or G.hn. The computer networks may also be embodied as one or more of the following types of networks: local area network (LAN); metropolitan area network (MAN); wide area network (WAN); virtual private network (VPN); storage area network (SAN); or global area network (GAN), among other network varieties.

For example, a WAN computer network may cover a broad area by linking communications across metropolitan, regional, or national boundaries. The network may use routers and/or public communication links. One type of data communication network may cover a relatively broad geographic area (e.g., city-to-city or country-to-country) which uses transmission facilities provided by common carriers, such as telephone service providers. In another example, a GAN computer network may support mobile communications across multiple wireless LANs or satellite networks. In another example, a VPN computer network may include links between nodes carried by open connections or virtual circuits in another network (e.g., the Internet) instead of by physical wires. The link-layer protocols of the VPN can be tunneled through the other network. One VPN application can promote secure communications through the Internet. The VPN can also be used to separately and securely conduct the traffic of different user communities over an underlying network. The VPN may provide users with the virtual experience of accessing the network through an IP address location other than the actual IP address which connects the access device to the network.

Computer networks may include hardware elements to interconnect network nodes, such as network interface cards (NICs) or Ethernet cards, repeaters, bridges, hubs, switches, routers, and other like components. Such elements may be physically wired for communication and/or data connections may be provided with microwave links (e.g., IEEE 802.12) or fiber optics, for example. A network card, network adapter or NIC can be designed to allow computers to communicate over the computer network by providing physical access to a network and an addressing system through the use of MAC addresses, for example. A repeater can be embodied as an electronic device that receives and retransmits a communicated signal at a boosted power level to allow the signal to cover a telecommunication distance with reduced degradation. A network bridge can be configured to connect multiple network segments at the data link layer of a computer network while learning which addresses can be reached through which specific ports of the network. In the network, the bridge may associate a port with an address and then send traffic for that address only to that port. In various embodiments, local bridges may be employed to directly connect local area networks (LANs); remote bridges can be used to create a wide area network (WAN) link between LANs; and/or, wireless bridges can be used to connect LANs and/or to connect remote stations to LANs.

In various embodiments, a hub may be employed which contains multiple ports. For example, when a data packet arrives at one port of a hub, the packet can be copied unmodified to all ports of the hub for transmission. A network switch or other devices that forward and filter OSI layer 2 datagrams between ports based on MAC addresses in data packets can also be used. A switch can possess multiple ports, such that most of the network is connected directly to the switch, or another switch that is in turn connected to a switch. The term "switch" can also include routers and bridges, as well as other devices that distribute data traffic by application content (e.g., a Web URL identifier). Switches may operate at one or more OSI model layers, including physical, data link, network, or transport (i.e., end-to-end). A device that operates simultaneously at more than one of these layers can be considered a multilayer switch. In certain embodiments, routers or other like networking devices may be used to forward data packets between networks using headers and forwarding tables to determine an optimum path through which to transmit the packets.

Embodiments of the methods and systems described herein may divide functions between separate CPUs, creating a multiprocessing configuration. For example, multiprocessor and multi-core (multiple CPUs on a single integrated circuit) computer systems with co-processing capabilities may be employed. Also, multitasking may be employed as a computer processing technique to handle simultaneous execution of multiple computer programs.

It will be appreciated that those skilled in the art will be able to devise various arrangements which, although not explicitly described or shown herein, embody the principles of the present disclosure and are comprised within the scope thereof. Furthermore, all examples and conditional language recited herein are principally intended to aid the reader in understanding the principles described in the present disclosure and the concepts contributed to furthering the art, and are to be construed as being without limitation to such specifically recited examples and conditions. Moreover, all statements herein reciting principles, aspects, and embodiments as well as specific examples thereof, are intended to encompass both structural and functional equivalents thereof. Additionally, it is intended that such equivalents comprise both currently known equivalents and equivalents developed in the future, i.e., any elements developed that perform the same function, regardless of structure. The scope of the present disclosure, therefore, is not intended to be limited to the exemplary aspects and aspects shown and described herein.

The various processes and techniques described herein may be implemented at least in part by software, comprising instructions that are stored or maintained by the computer-readable memory of the access device, the host computing device, and/or of any other device, or by independent computer-readable memory that is used for storing and transferring the software.

Although the flow charts and methods described herein may describe a specific order of execution, it is understood that the order of execution may differ from that which is described. For example, the order of execution of two or more blocks or steps may be scrambled relative to the order described. Also, two or more blocks or steps may be executed concurrently or with partial concurrence. Further, in some embodiments, one or more of the blocks or steps may be skipped or omitted. It is understood that all such variations are within the scope of the present disclosure.

What is claimed is:

1. A system for characterizing indoor air quality in a particular building having multiple locations therein, the system comprising:
   a back-end data center that comprises one or more computer servers;
   outdoor air quality sensor means located outside and not inside the particular building, wherein the outdoor air quality sensor means is in communication with the data center via the computer network and transmits time-stamped air quality readings collected by the outdoor air quality sensor means to the back-end data center via the computer network;
   indoor air quality sensor means located inside the particular building, wherein the indoor air quality sensor means transmits time-stamped air quality readings collected by the indoor air quality sensor means to the back-end data center via a computer network; and
   a graphical display means that is in communication with the back-end data center via the computer network,
   wherein:
   the back-end data center computes spatiotemporal air quality measures for the building based on at least the time-stamped air quality readings from the indoor air quality sensor means and the time-stamped air quality readings from the outdoor sensor means, wherein the back-end data center computes raw, time-stamped air quality measures for a particular location in the particular building at a particular time stamp by performing one or more steps that comprise subtracting (i) the air quality reading from the indoor air quality sensor means at the time stamp when located in the particular location in the particular building, from (ii) the air quality reading from the outdoor air quality sensor means at the time stamp, and wherein the spatiotemporal air quality measures computed by the back-end data center comprise statistical summarizations of the raw, time-stamped air quality measures over rolling time periods;

the back-end data center transmits the spatiotemporal air quality measures to the graphical display means via the computer network; and the graphical display means displays the spatiotemporal air quality measures computed by the back-end data center on an interactive graphical display of the graphical display device.

2. A method for characterizing indoor air quality in a particular building having multiple locations therein, the method comprising:

receiving, via a computer network, by a back-end data center that comprises one or more computer servers that are connected to the computer network, from at least one indoor air quality sensor located inside the particular building, time-stamped air quality readings collected by the at least one indoor air quality sensor;

receiving, by the data center, via the computer network, from at least one outdoor air quality sensor location outside and not inside the particular building, time-stamped air quality readings collected by the at least one outdoor air quality sensor;

computing, by the data center, spatiotemporal air quality measures for the particular building based on at least the time-stamped air quality readings from the at least one indoor air quality sensor and the time-stamped air quality readings from the at least one outdoor air quality sensor, wherein the data center computes raw, time-stamped air quality measures for a particular location in the particular building at a particular time stamp by performing one or more steps that comprise subtracting (i) the air quality reading from the at least one indoor air quality sensor at the time stamp when located in the particular location in the particular building, from (ii) the air quality reading from the at least one outdoor air quality sensor at the time stamp, and wherein the spatiotemporal air quality measures computed by the data center comprise statistical summarizations of the raw, time-stamped air quality measures over rolling time periods; and transmitting, by the back-end data center, via the computer network, the spatiotemporal air quality measures to a graphical display device for display of the spatiotemporal air quality measures computed by the back-end data center on an interactive graphical display of the graphical display device.

3. The method of claim 2, further comprising the back-end data center computing and transmitting to the graphical display device, a mean air pollution recovery index value for the particular building by performing steps that comprise:

identifying several local particle count maxima in the time-stamped air quality readings from the at least one indoor air quality sensor over a time period;

computing a post-maximum recovery slope for each of the several local particle count maxima to an immediately subsequent minimum particle count;

computing a mean of the post-maximum recovery slopes across all of the several local particle count maxima in the time period; and transmitting the mean post-maximum recovery slope to the graphical display device.

4. The method of claim 2, further comprising the back-end data center:

continuously computing real-time air quality measures for the particular building based on the time-stamped air quality readings from the at least one indoor air quality sensor; and transmitting a notification to the graphical display device via the computer network when a real-time air quality measure exceeds a pre-established threshold.

5. A system for characterizing indoor air quality in a particular building having multiple locations therein, the system comprising:

a back-end data center that comprises one or more computer servers;

at least one indoor air quality sensor located inside the particular building, wherein the at least one indoor air quality sensor transmits time-stamped air quality readings collected by the at least one indoor air quality sensor to the data center via a computer network;

at least one outdoor air quality sensor that is located outside and not inside the particular building, wherein the at least one outdoor air quality sensor is in communication with the data center via the computer network; and a graphical display device, wherein:

the data center computes spatiotemporal air quality measures for the particular building based on at least the time-stamped air quality readings from the at least one indoor air quality sensor and the time-stamped air quality readings from the at least one outdoor air quality sensor, wherein the data center computes raw, time-stamped air quality measures for a particular location in the particular building at a particular time stamp by performing one or more steps that comprise subtracting (i) the air quality reading from the at least one indoor air quality sensor at the time stamp when located in the particular location in the particular building, from (ii) the air quality reading from the at least one outdoor air quality sensor at the time stamp, and wherein the spatiotemporal air quality measures computed by the data center comprise statistical summarizations of the raw, time-stamped air quality measures over rolling time periods;

the data center transmits the spatiotemporal air quality measures to the graphical display device via the computer network; and the graphic display device displays the spatiotemporal air quality measures computed by the data center on an interactive graphical display of the graphical display device.

6. The system of claim 5, wherein the air quality readings from the at least one indoor air quality sensor comprise PM2.5 readings.

7. The system of claim 5, wherein the single graphical display device is combined with the at least one indoor air quality sensor in a composite air quality sensor/display device.

8. The system of claim 5, wherein:

the graphical display device comprises a network-enabled computer device that is selected from the group consisting of a personal computer, a laptop, a smartphone, a table computer, and a wearable computer device; and the network-enabled computer device is in communication with the back-end data center for receiving and displaying the spatiotemporal air quality measures transmitted via the computer network to the network-enabled computer device.

9. The system of claim 8, wherein:
the back-end data center receives data annotations from a user from the graphical display device via the computer network, wherein the data annotations comprises data pertaining to the at least one air quality sensor; and
the data annotations are displayed by the graphical display device.

10. The system of claim 5, wherein the back-end data center further computes and transmits to the graphical display device a mean air pollution recovery index value for the particular building by performing steps that comprise:
identifying several local particle count maxima in the time-stamped air quality readings from the at least one indoor air quality sensor over a time period;
computing a post-maximum recovery slope for each of the several local particle count maxima to an immediately subsequent minimum particle count;
computing a mean of the post-maximum recovery slopes across all of the several local particle count maxima in the time period; and
transmitting the mean post-maximum recovery slope to the graphical display device.

11. The system of claim 5, wherein the back-end data center further computes and transmits to the graphical display device a median air pollution recovery index value for the particular building by performing steps that comprise:
identifying several local particle count maxima in the time-stamped air quality readings from the at least one indoor air quality sensor over a time period;
computing a post-maximum recovery slope for each of the several local particle count maxima to an immediately subsequent minimum particle count;
computing a median of the post-maximum recovery slopes across all of the several local particle count maxima in the time period; and
transmitting the median post-maximum recovery slope to the graphical display device.

12. The system of claim 5, wherein:
the at least one indoor air quality sensor comprises at least first and second indoor air quality sensors;
the first indoor air quality sensor is located in a first location in the particular building;
the second indoor air quality sensor is located in a second location in the particular building; and
the spatiotemporal air quality measures computed by the back-end data center comprise air quality measures from the first and second locations.

13. The system of claim 5, wherein:
the at least one indoor air quality sensor comprises a first indoor air quality sensor that is located in a first location in the particular building for a first time period and is located in a second location in the particular building for a second time period; and
the spatiotemporal air quality measures computed by the back-end data center comprise air quality measures from the first and second locations.

14. The system of claim 5, wherein the back-end data center:
continuously computes real-time air quality measures for the particular building based on the time-stamped air quality readings from the at least one indoor air quality sensor; and
transmits a notification to the graphical display device via the computer network when a real-time air quality measure exceeds a pre-established threshold.

15. A system for characterizing indoor air quality in a particular building having multiple locations therein, the system comprising:
a back-end data center that comprises one or more computer servers;
at least one indoor air quality sensor located inside the particular building, wherein the at least one indoor air quality sensor transmits time-stamped air quality readings collected by the at least one indoor air quality sensor to the data center via a computer network; and
a graphical display device, wherein:
the data center computes a mean air pollution recovery index value for the particular building by performing steps that comprise:
identifying several local particle count maxima in the time-stamped air quality readings from the at least one indoor air quality sensor over a time period;
computing a post-maximum recovery slope for each of the several local particle count maxima to an immediately subsequent minimum particle count; and
computing a mean of the post-maximum recovery slopes across all of the several local particle count maxima in the time window;
the data center transmits the mean air pollution recovery index value to the graphical display device via the computer network; and
the graphic display device displays the s mean air pollution recovery index value computed by the data center on an interactive graphical display of the graphical display device.

16. A system for characterizing indoor air quality in a particular building having multiple locations therein, the system comprising:
a back-end data center that comprises one or more computer servers;
at least one indoor air quality sensor located inside the particular building, wherein the at least one indoor air quality sensor transmits time-stamped air quality readings collected by the at least one indoor air quality sensor to the data center via a computer network; and
a graphical display device, wherein:
the data center computes a median air pollution recovery index value for the particular building by performing steps that comprise:
identifying several local particle count maxima in the time-stamped air quality readings from the at least one indoor air quality sensor over a time period;
computing a post-maximum recovery slope for each of the several local particle count maxima to an immediately subsequent minimum particle count;
computing a median of the post-maximum recovery slopes across all of the several local particle count maxima in the time window; and
the data center transmits the median of the post-maximum recovery slopes to the graphical display device via the computer network; and
the graphic display device displays the median of the post-maximum recovery slopes computed by the data center on an interactive graphical display of the graphical display device.

17. A method for characterizing indoor air quality in a particular building having multiple locations therein, the method comprising:
receiving, via a computer network, by a back-end data center that comprises one or more computer servers that are connected to the computer network, from at least one indoor air quality sensor located inside the particular building, time-stamped air quality readings collected by the at least one indoor air quality sensor;

computing, by the data center, a median air pollution recovery index value for the particular building based on at least the time-stamped air quality readings from the at least one indoor air quality sensor by performing steps that comprise:

identifying several local particle count maxima in the time-stamped air quality readings from the at least one indoor air quality sensor over a time period;

computing a post-maximum recovery slope for each of the several local particle count maxima to an immediately subsequent minimum particle count;

computing a mean of the post-maximum recovery slopes across all of the several local particle count maxima in the time window; and transmitting, by the data center, via the computer network, the mean of the post-maximum recovery slopes to a graphical display device for display of the mean of the post-maximum recovery slopes computed by the data center on an interactive graphical display of the graphical display device.

\* \* \* \* \*